United States Patent [19]

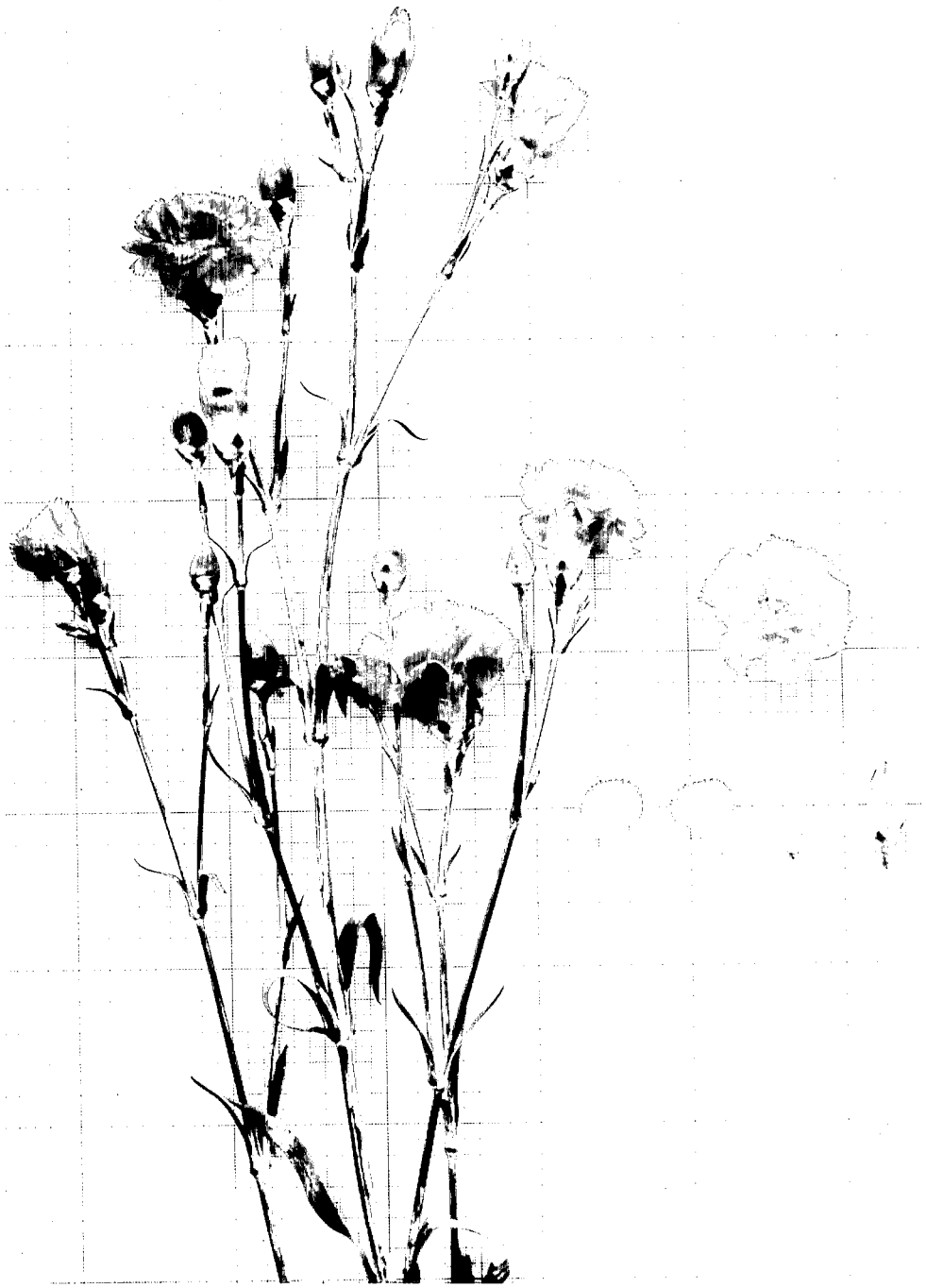

Hilverda

[11] Patent Number: Plant 5,754

[45] Date of Patent: Jun. 24, 1986

[54] CARNATION NAMED HILREBA

[75] Inventor: Jan J. Hilverda, Aalsmeer, Netherlands

[73] Assignee: Hilverda B.V., Aalsmeer, Netherlands

[21] Appl. No.: 674,759

[22] Filed: Nov. 26, 1984

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Chas. W. Rummler

[57] ABSTRACT

A new spray carnation variety having small flowers of a generally Turkey Red color which are produced profusely and continuously on strong, tall, flowering stems, the plant being additionally distinguished by its disease resistance and by a rapid and vigorous growth habit reaching about one meter in height.

1 Drawing Figure

BACKGROUND OF THE NEW PLANT

This new carnation cultivar originated as a sport of the variety "Hilbar" (U.S. Plant Pat. No. 5,574) growing in nursery at Aalsmeer, Holland, this sport being selected for propagation because of the deeper Turkey Red color of its flowers compared to the much lighter Rose Bengal color of the flowers of the parent plant. Propagation of this sport was carried on by me at Aalsmeer, Holland, by means of cuttings, and since the propagated plants appeared to have retained all of the advantageous physiological characteristics of the parent plant, propagation by cuttings was continued through several successive generations, which demonstrated that the distinguishing characteristics of the new plant were apparently fixed and would hold true from generation to generation thereby providing a new plant having very favorable prospects for commercialization.

DESCRIPTION OF THE DRAWING

My new spray carnation cultivar is illustrated by the accompanying photographic drawing which shows, in full color, typical stems of the new plant bearing buds in various stages and fully opened flowers, the drawing also including a face view of a single fully opened bloom, together with front and reverse sides of flower petals, the colors shown being as true as is reasonably possible to obtain by conventional photographic procedures.

DESCRIPTION OF THE NEW PLANT

The following is a detailed description of my new carnation plant based upon observations of greenhouse grown plants at Aalsmeer, Holland, in the summer of 1984, the color designations being according to The R.H.S. Colour Chart published by The Royal Horticultural Society of London, England.

THE PLANT

Origin: Sport.

Parentage: Spray carnation variety "Hilbar" (U.S. Plant patent application Ser. No. 559,360 filed Dec. 8, 1983).

Classification:

*Botanic.*—*Dianthus caryophyllus L.*

*Commercial.*—Spray carnation.

Form: Tall, spray shaped bush.

Height: Approximately one meter.

Growth habit: Vigorous, rapid, upright and strong.

Branching character: Alternate.

Foliage:

*Quantity.*—Abundant.

*Size of leaf.*—Approximately 10 to 12 cm. long.

*Shape of leaf.*—Sessile, lanceolate and with smooth margins.

*Texture.*—Leathery.

*Color.*—Upper side — Blue-Green. Under side — Blue-Green.

*Ribs and veins.*—The midrib is prominent.

*Leaflets.*—None.

THE BUD

Size: Medium

*Diameter.*—About 12 to 15 mm.

*Length.*—About 20 to 30 mm.

Form: Oval shaped and pointed.

Opening rate: When the bud is mature, flowers will appear about five days later.

Color:

*When sepals first divide.*—Red.

*When petals begin to unfurl.*—Turkey Red with Claret Rose base.

Sepals: Hooded over the bud and remaining upstanding when the flowers open.

*Shape.*—Generally oblong with blunt base and acute apex.

*Color.*—Inside — Light Green. Outside — Dark Green.

Calyx:

*Shape.*—Funnel-shaped.

*Size.*—Medium.

*Aspect.*—Smooth.

*Splitting.*—The calyx does not split.

Flower stem:

*Length.*—Approximately 50 cm.

*Character.*—Erect and rigid.

*Color.*—Dark Green.

THE FLOWER

Blooming habit: Continuous and profuse.

Size of bloom: Small.

*Diameter.*—Approximately 55 mm.

*Depth.*—Approximately 25 mm.

Borne: In cluster with more than three flowers per stem.

Shape: When bloom first opens, high center. When bloom matures, it flattens.

Petalage:

*Number of petals.*—26.

*Arrangement.*—Imbricated.

*Form.*—Fan-shaped with dentated margin.

*Texture.*—Soft.

*Appearance.*—Velvety.

*Color.*—All petals — Turkey Red, R.H.S. 46C, with base portion of Claret Rose, R.H.S. 50A.

Petaloids:

*Number.*—26.

Flower stem:

*Length.*—About 50 to 60 cm.

*Character.*—Upright and sturdy.

*Color.*—Dark Green.

Persistence: The petals hang on and dry.

Disease resistance: Resistant to *Fusarium oxysporum* and *Fusarium rodolens* as observed growing in The Netherlands.

Fragrance: Weak.

Lasting quality:

*As cut flower.*—10 to 14 days.

REPRODUCTIVE ORGANS

Stamens: Normal in number and evenly arranged.

*Anthers.*—Size: Normal. Color: Cream.

*Filaments.*—Length: About 10 to 20 mm. Color: White. *Pollen.*—Color: White.

Pistils:

*Number.*—Not more than three.

*Styles.*—Length: Approximately 20 mm. Color: White.

*Stigmas.*—Color: White with reddish top.

Ovaries: Of cylindrical shape, light green with white base, smooth aspect and slightly ribbed.

In general, this new spray carnation cultivator has all of the principal characteristics of the parent plant excepting that the flowers are of a much darker coloration than the flowers of the parent.

I claim:

1. A new and distinct spray carnation cultivar, substantially as herein shown and described, characterized by its profuse and continuous production of small flowers of a Turkey Red color.

* * * * *